United States Patent
Breedvelt-Schouten et al.

(10) Patent No.: US 11,163,822 B2
(45) Date of Patent: *Nov. 2, 2021

(54) EMOTIONAL EXPERIENCE METADATA ON RECORDED IMAGES

(71) Applicant: International Business Machines Corporation, Armonk, NY (US)

(72) Inventors: Ilse M. Breedvelt-Schouten, Manotick (CA); Jana H. Jenkins, Raleigh, NC (US); Jeffrey A. Kusnitz, Campbell, CA (US); John A. Lyons, Ottawa (CA)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/525,718

(22) Filed: Jul. 30, 2019

(65) Prior Publication Data

US 2020/0285669 A1 Sep. 10, 2020

Related U.S. Application Data

(63) Continuation of application No. 16/293,812, filed on Mar. 6, 2019.

(51) Int. Cl.
*G06K 9/00* (2006.01)
*G06F 16/583* (2019.01)
(Continued)

(52) U.S. Cl.
CPC .............. *G06F 16/583* (2019.01); *A61B 5/16* (2013.01); *G06F 16/783* (2019.01); *G06K 9/00302* (2013.01)

(58) Field of Classification Search
CPC .................................................. G06K 9/00302
See application file for complete search history.

(56) References Cited

U.S. PATENT DOCUMENTS 3,691,652 A * 9/1972 Clynes ..................... A61B 5/16
434/236
5,305,423 A * 4/1994 Clynes ..................... A61B 5/16
704/258

(Continued)

OTHER PUBLICATIONS

Emotional maps—similarity, Soheila Ashkezari et al., ELSEVIER, Mar. 2019, pp. 113-124 (Year: 2019).*

(Continued)

*Primary Examiner* — Jayesh A Patel
(74) *Attorney, Agent, or Firm* — Nicholas A. Welling; Alexander G. Jochym

(57) ABSTRACT

Provided are techniques for enhancing images with emotion information, comprising capturing a plurality of images; identifying an individual in the plurality of images; analyzing the plurality of images for emotional content; converting the emotional content into emotion metadata; correlating the emotional content with the individual to produce associated emotion metadata; and storing the associated emotion metadata in conjunction with the captured image in a computer-readable storage medium. The disclosed techniques may also include capturing physiological data corresponding to an individual that captures the image; analyzing the physiological data for a second emotional content; converting the second emotional content into a second emotion metadata; storing the second emotion metadata in conjunction with the captured image in the computer-readable storage medium.

4 Claims, 5 Drawing Sheets

(51) Int. Cl.
*A61B 5/16* (2006.01)
*G06F 16/783* (2019.01)

(56) References Cited

U.S. PATENT DOCUMENTS

| | | | | |
|---|---|---|---|---|
| 7,010,144 B1* | 3/2006 | Davis | ............... | G06T 1/0021 382/100 |
| 7,171,113 B2* | 1/2007 | Parulski | ............. | G06F 16/58 396/287 |
| 7,577,310 B2* | 8/2009 | Kinjo | ............. | G06K 9/00221 382/118 |
| 8,654,937 B2* | 2/2014 | Agapi | ............. | H04M 3/5175 379/88.09 |
| 9,081,801 B2 | 7/2015 | Lyons | | |
| 9,202,251 B2* | 12/2015 | Bist | ............. | G06F 16/436 |
| 9,560,411 B2* | 1/2017 | Seo | ............. | H04N 21/44218 |
| 9,648,171 B1* | 5/2017 | Eftekhari | ............. | G06Q 30/016 |
| 9,807,298 B2 | 10/2017 | Kim | | |
| 2003/0108241 A1* | 6/2003 | Colmenarez | ....... | H04N 1/00127 382/181 |
| 2003/0118974 A1* | 6/2003 | Obrador | ............. | G09B 23/28 434/236 |
| 2003/0156304 A1* | 8/2003 | Fedorovskaya | .... | G06K 9/00315 358/527 |
| 2004/0095344 A1* | 5/2004 | Dojyun | ............. | G06T 13/40 345/419 |
| 2005/0159958 A1* | 7/2005 | Yoshimura | ......... | G06K 9/00335 704/276 |
| 2006/0281064 A1* | 12/2006 | Sato | ............. | G09B 23/286 434/308 |
| 2007/0033050 A1* | 2/2007 | Asano | ............. | G06F 16/436 704/270 |
| 2007/0121824 A1* | 5/2007 | Agapi | ............. | H04M 3/5175 379/88.18 |
| 2007/0208569 A1* | 9/2007 | Subramanian | ...... | G10L 19/0018 704/270 |
| 2008/0002892 A1* | 1/2008 | Jelonek | ............. | H04N 21/812 382/224 |
| 2009/0002178 A1* | 1/2009 | Guday | ............. | G06F 3/0346 340/573.1 |
| 2009/0021380 A1* | 1/2009 | Higuchi | ............. | G01D 21/00 340/573.1 |
| 2009/0051826 A1* | 2/2009 | Chang | ............. | G11B 27/105 348/744 |
| 2009/0144366 A1* | 6/2009 | Lyle | ............. | G06Q 10/107 709/204 |
| 2010/0086204 A1* | 4/2010 | Lessing | ............. | G06F 16/58 382/165 |
| 2010/0211966 A1* | 8/2010 | Zhang | ............. | H04N 21/4223 725/10 |
| 2011/0040155 A1* | 2/2011 | Guzak | ............. | A61B 5/16 600/300 |
| 2011/0184950 A1* | 7/2011 | Skaff | ............. | G06K 9/00664 707/737 |
| 2012/0155773 A1* | 6/2012 | Tsukamoto | ......... | G06K 9/00302 382/190 |
| 2012/0233531 A1* | 9/2012 | Ma | ............. | G11B 27/322 715/205 |
| 2012/0272160 A1* | 10/2012 | Spivack | ............. | H04L 51/32 715/752 |
| 2014/0029854 A1* | 1/2014 | Lyons | ............. | G06F 16/58 382/190 |
| 2014/0074945 A1* | 3/2014 | Kanevsky | ............. | H04L 51/12 709/206 |
| 2014/0154649 A1* | 6/2014 | Farley | ............. | A61B 5/6898 434/236 |
| 2014/0192229 A1* | 7/2014 | Kim | ............. | H04N 1/32128 348/231.3 |
| 2015/0018023 A1* | 1/2015 | Tomii | ............. | G06F 40/30 455/466 |
| 2015/0032771 A1* | 1/2015 | Berio | ............. | G06Q 50/01 707/769 |
| 2015/0178915 A1* | 6/2015 | Chatterjee | ............. | G06F 16/58 382/128 |
| 2016/0063874 A1* | 3/2016 | Czerwinski | ......... | G06Q 10/107 434/236 |
| 2016/0078279 A1* | 3/2016 | Pitre | ............. | A61B 5/165 382/118 |
| 2016/0123743 A1* | 5/2016 | Sisbot | ............. | G01C 21/3461 701/538 |
| 2016/0210115 A1* | 7/2016 | Lee | ............. | G06F 3/167 |
| 2017/0046496 A1* | 2/2017 | Johnstone | ............. | G06F 16/2228 |
| 2017/0105048 A1* | 4/2017 | Stein | ............. | G06F 3/0482 |
| 2017/0339338 A1* | 11/2017 | Gordon | ............. | G06K 9/00597 |
| 2017/0351417 A1* | 12/2017 | Manico | ............. | G06F 16/50 |
| 2017/0364484 A1* | 12/2017 | Hayes | ............. | G06F 40/109 |
| 2018/0077095 A1* | 3/2018 | Deyle | ............. | G10L 25/63 |
| 2018/0176641 A1* | 6/2018 | Yun | ............. | H04N 21/44016 |
| 2018/0350144 A1* | 12/2018 | Rathod | ............. | G06Q 20/3276 |
| 2019/0007350 A1* | 1/2019 | Koukoumidis | ......... | H04L 51/02 |
| 2019/0122071 A1* | 4/2019 | Jin | ............. | G06K 9/00302 |
| 2020/0285668 A1 | 9/2020 | Breedvelt-Schouten | | |

OTHER PUBLICATIONS

Engineering Applications of Artificial Intelligence, A. Kaklauskas et al., ELSEVIER, 0952-1976, 2011, pp. 928-945 (Year: 2011).*

Evaluating Instantaneous Psychological Stress from Emotional Composition of a Facial Expression, Suvashis Das et al., Journal of Advanced Computational Intelligence and Intelligence Informatics, vol. 17 No. 4, 2013, pp. 480-492 (Year: 2013).*

Thermal Image Analysis for Polygraph Testing, Ioannis Pavlidis et al., IEEE Engineering in Medicine and Biology Nov./Dec. 2002, pp. 56-64 (Year: 2002).*

Managing Personal Health Records Using Meta-Data and Cloud Storage., Mohammed Abdulkareem Alyami et al., IEEE, 978-1-5090-5507-4, 2017, pp. 265-271 (Year: 2017).*

Ark, "The Emotional Mouse," Proceedings of HCI International (the 8th International Conference on Human-Computer Interaction) on Human-Computer Interaction: Ergonomics and User Interfaces—vol. I—vol. I pp. 818-823, Aug. 22-26, 1999.

Tkalcic, "Affective Labeling in a Content-Based Recommender System for Images," IEEE Transactions on Multimedia, vol. 15, No. 2, Feb. 2013.

Photometadata.org, "Meta 101: Metadata Q&A,", downloaded from <http://www.photometadata.org/META-101-metadata-Q-and-A> on Mar. 6, 2019.

"Welcome to the Eyeris EmoVu SDK Documentation," downloaded from <http://emovu.com/docs/html/getting_started.htm> on Mar. 6, 2019.

Graham, "Build a custom language model for Watson speech to text," IBM Developer Day, Bengaluru, Jul. 6, 2018.

Schuller, "Automatic Recognition of Emotion Evoked by General Sound Events," International Conference on Acoustics, Speech, and Signal Processing, pp. 341-344, 2012.

Martinelli, "Create a mobile app that analyzes the emotions of content," IBM Developer Day, Bengaluru, Dec. 13, 2018.

Breedvelt-Schouten et al., "Emotional Experience Metadata on Recorded Images", IBM U.S. Appl. No. 16/293,812, filed Mar. 6, 2019, pp. 1-20.

IBM Appendix P., "List of IBM Patents or Patents to be Treated as Related", Dated Herewith, 2 pages.

* cited by examiner

EMOTIONAL EXPERIENCE METADATA ON RECORDED IMAGES

CROSS-REFERENCES TO RELATED APPLICATIONS

The present application is a continuation and claims the benefit of the filing date of an application entitled, "Emotional Experience Metadata on Recorded Images" Ser. No. 16/293,812, filed Mar. 6, 2019, assigned to the assignee of the present application, and herein incorporated by reference

FIELD OF DISCLOSURE

The claimed subject matter relates generally to stored images and, more specifically, to the inclusion of metadata corresponding to an emotional state in a stored image or images.

BACKGROUND OF THE INVENTION

Each time a picture or video is captured and stored in a non-transitory, computer-readable storage medium, metadata associated with the picture or video may also be stored. Examples of metadata include technical, descriptive and administrative metadata. Some examples of technical metadata include size, color profile, ISO speed and camera settings. Some examples of descriptive metadata include captions, headings, titles, keywords and location of capture. Examples of administrative metadata include licensing, creator name and contact information. Such metadata may be employed to objectively analyze the picture or video Pictures and videos may also be analyzed subjectively. Subjective analysis typically involves the meaning that a person may derive from the picture or image. This meaning can be stored in conjunction with tags or comments provided with the image. For example, on FACEBOOK®, pictures are consumed by users and get comments and tags as the users derive meaning from the pictures.

SUMMARY

As the Inventors herein have realized, there is currently no way to store an emotional state of subjects in a picture or video just immediately before, during or after the picture is taken. Such information would be useful to further enhance future utility of the stored picture or video.

The claimed subject matter records a multitude of physical characteristics within an image or video to measure emotions associated with either or both of the person taking the photograph or a person or persons being photographed. Emotion information is then added to the stored image or video as metadata associated with the image. The disclosed technology enables stored images to be filtered and retrieved based upon the stored emotion metadata, thereby enhancing the experience of consuming and analyzing images and videos by applying filters associated with emotional states.

Provided are techniques for enhancing images with emotion information, comprising capturing a plurality of images; identifying an individual in the plurality of images; analyzing the plurality of images for emotional content; converting the emotional content into emotion metadata; correlating the emotional content with the individual to produce associated emotion metadata; and storing the associated emotion metadata in conjunction with the captured image in a computer-readable storage medium.

The disclosed techniques may also include capturing physiological data corresponding to an individual that captures the image; analyzing the physiological data for a second emotional content; converting the second emotional content into a second emotion metadata; storing the second emotion metadata in conjunction with the captured image in the computer-readable storage medium.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures, in which:

DETAILED DESCRIPTION

Figure 1:
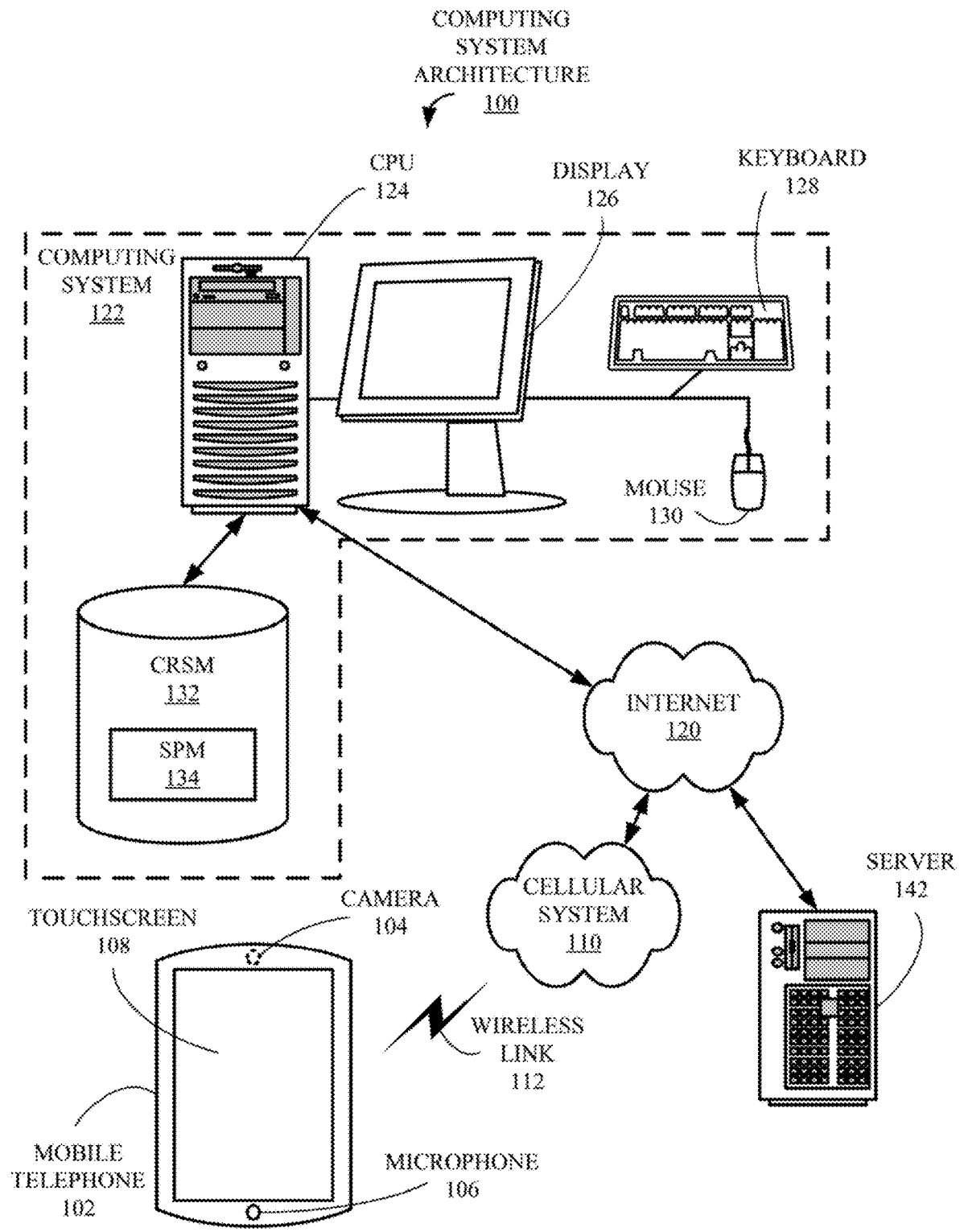
FIG. 1 is a computing architecture that may support the claimed subject matter.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PEA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Turning now to the figures, FIG. 1 is a block diagram of an example of a computing architecture 100 that may implement the claimed subject matter. A mobile telephone 102, which may also be referred to as a "smartphone," includes a camera 104, only a lens of which is visible, a microphone 106 and a touchscreen 108. Camera 104 is represented with dotted lines of the lens because the lens may be located on the back, or obscured side, of telephone 102 rather than the side of telephone 102 visible in FIG. 1.

Smartphone 102 is connected to a cellular system 110 via a wireless link 112. Cellular system 112 is connected to a network, which in this example is the Internet 120. Internet 120 is coupled to a computing system 122. Although in the rest of the Specification, telephone 102 is described as including the technology necessary to implement the claimed subject matter, computing system 122 is used as an example of a system that might be employed for off-line processing. Also coupled to the Internet 120 is a server 142 that also might be employed for off-line processing and would typically include many or all the illustrated components of computing system 122. Computing system 122 and server 142 may also be employed for the storage and retrieval of images and videos produced in accordance with the claimed subject matter.

Computing system 122 includes a central processing unit (CPU) 124, coupled to a display 126, a keyboard 128 and a pointing device, or "mouse," 130, which together facilitate human interaction with elements of architecture 100 and computing system 122. CPU 124 may include a plurality of processors (not shown). Also included in computing system 122 and attached to CPU 124 is a computer-readable storage medium (CRSM) 132, which may either be incorporated into CPU 124 i.e. an internal device, or attached externally to CPU 124 by means of various, commonly available connection devices such as but not limited to, a universal serial bus (USB) port (not shown). CRSM 132 is illustrated storing logic associated with a Sensor Processing Module (SPM) 134, which would be responsible for implementing off-line processing of the disclosed technology.

It should be understood that although the disclosed technology is described with respect to mobile telephone 102 many other types of devices may include the claimed subject matter, including, but not limited to, a notebook computer, tablet computer, smart watch, sound recording device and so on.

Figure 2:
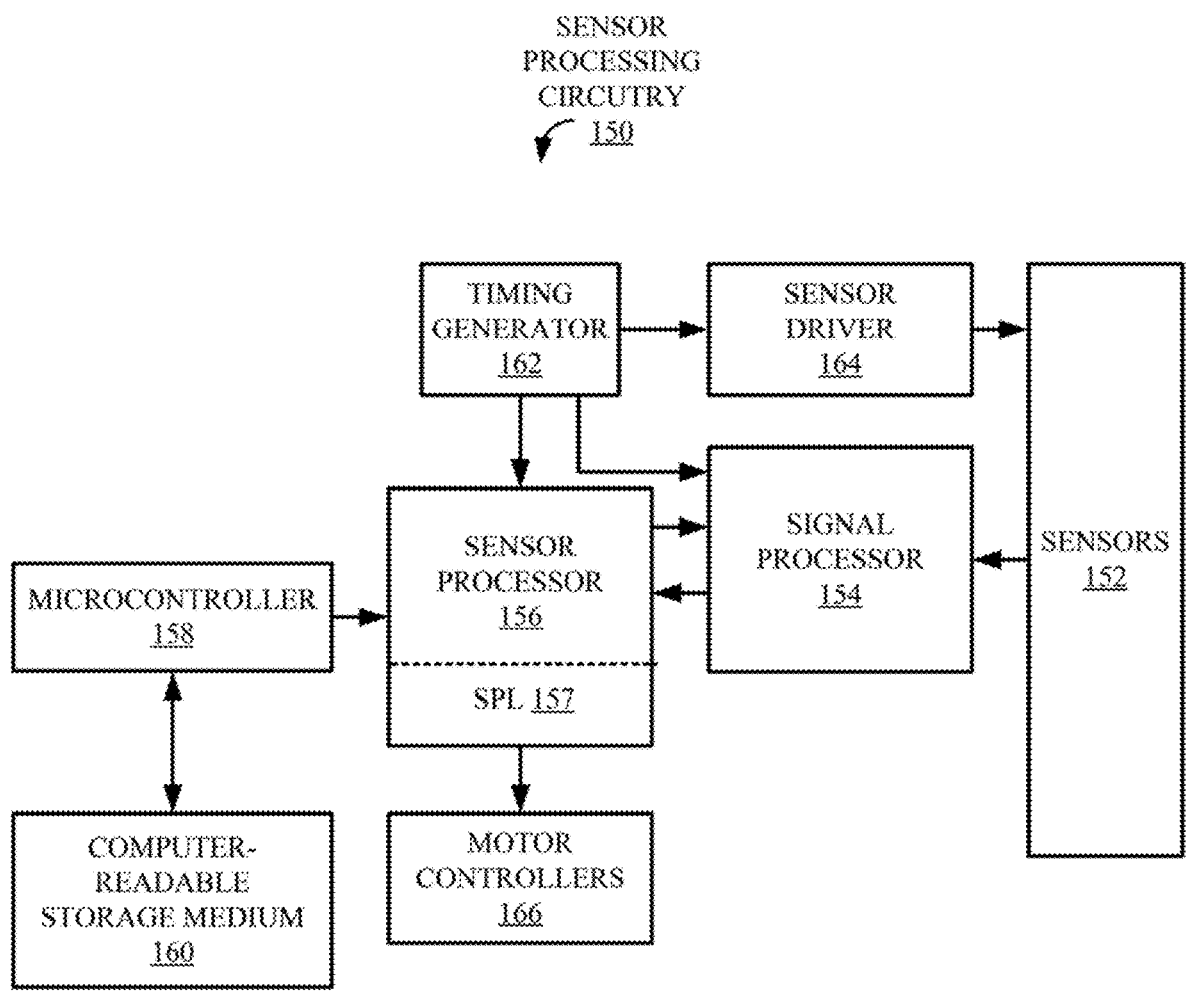
FIG. 2 is a block diagram of sensor processing circuitry that may implement aspects of the claimed subject matter.

FIG. 2 is a block diagram of a one example of sensor processing circuitry, or simply "circuitry," 150 that may be associated with telephone 102 of FIG. 1. Circuitry 150 includes sensors 152, which would include camera 104, microphone 106 and touch screen 108, all of which were introduced in FIG. 1. Sensors 152 may also include instruments for the collection of such attributes as finger pressure, heart rate, skin temperature, skin electricity, skin conductivity, moisture and potentially other physical characteristics. In one embodiment, touch screen 108 includes the capability to measure and collect some of such data.

An image captured by a camera 104, sound captured by microphone 106 and attributes such as finger pressure, heart rate, skin temperature and skin electricity captured by touch screen 108 are processed by sensors 152, which transmits a signal to a signal processor 154. After processing the transmitted signal, signal processor 154 transmits a digital signal corresponding to the captured attributes to a sensor processor 156. In accordance with the claimed subject matter, sensor processor 156 includes Sensor Processing Logic (SPL) 157. Although illustrated in conjunction with image processor 156, all or parts of SPL 157 may be implemented as one or more separate components of telephone 122. Some processing associated with SPL 157 may even be configured to take place on devices other than telephone 102 such as computing system 122 (FIG. 1) or server 142 (FIG. 1) in a post processing configuration.

Processing associated with SPL 157 is described in more detail below in conjunction with FIGS. 3 and 4. Sensor processor 156 is controlled by a microcontroller 158, which is coupled to a computer-readable storage medium (CRSM 160, and a timing generator 162 and in turn controls motor controllers 166. Motor controllers 166 controls mechanical aspects of telephone 102, such as, but not limited to, a shutter (not shown) that allows light to hit camera 104.

Timing generator 162 signals a sensor driver 164 that is used to control sensor capture timing by sensors 152 and coordinates activities of sensors 152 and signal processor 154. It should be understood that circuitry 150 is used for the purposes of illustration only and that a typical mobile telephone would be much more complex with either additional or different components. In addition, the claimed subject matter is also applicable to other types of devices such as, but not limited to, video cameras, smart phones and table computers, any one of which may include different types of sensors to capture the data necessary to implement the claimed subject matter. For example, a smartwatch may include an attachment that clips on a finger to measure heartrate, temperature and other physiological measurements.

Figure 3:
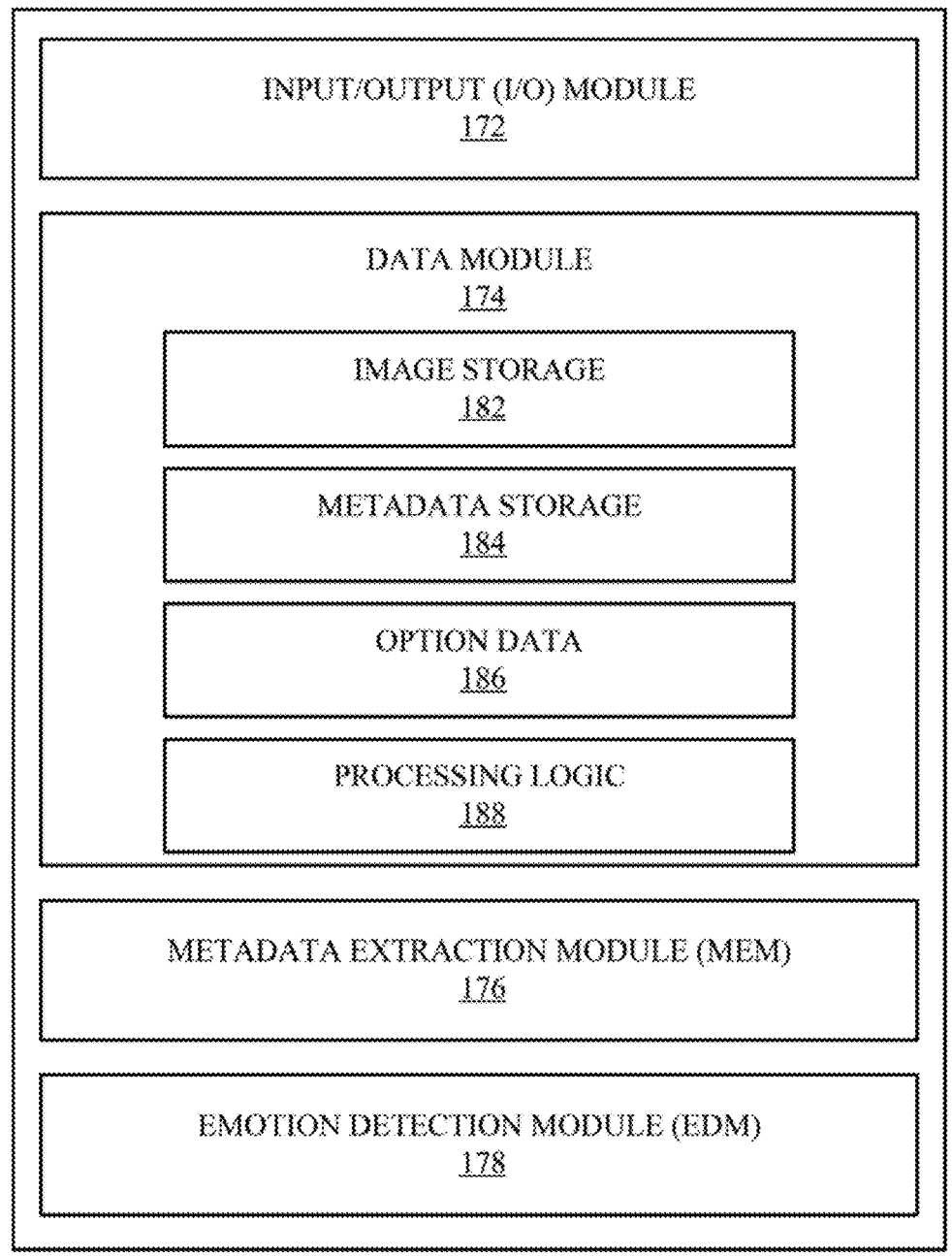
FIG. 3 is a block diagram of Sensor Processing Logic that may implement aspects for the claimed subject matter.

FIG. 3 is a block diagram of SPL 157, described above in conjunction with FIG. 2, in greater detail. SPL 157 includes an input/output (I/O) module 172, a data module 174, a metadata extraction module (MEM) 176 and an emotion detection module (EDM) 178. It should be understood that the claimed subject matter can be implemented in many types of software and circuitry but, for the sake of simplicity, is described only in terms of smartphone 102 (FIG. 1), camera 104 (FIG. 1) and SPL 157. Further, the representation of SPL 157 in FIG. 3 is a logical model. In other words, components 172, 174 and 178 may be implemented in software or hardware and configured in many types of devices and configurations, as will be apparent to one with skill in the relevant arts.

I/O module 172 handles any communication SPL 157 has with other components of smartphone 102. Data module 172 stores information that SPL 157 requires during normal operation. Examples of the types of information stored in data module 172 include image storage 182, metadata storage 184, option data 186 and processing logic 188. Image storage 182 provides storage for both images and videos captured by camera 104 (FIG. 1). Metadata storage 184 stores information extracted from processing associated with any captured image and physiological measurements captured by sensors 152. Option data 186 stores information that control the operation of SPL 157, including, but not limited to, storage locations and file storage formats. Processing logic 188 stores the code that controls the operation of SPL 157, subject to the configuration parameters stored in option data 186.

Metadata Extraction module 176 extracts information from the image. Such information may include technical, descriptive and administrative metadata as well as any emotion metadata that may be apparent. Emotion Detection module (EDM) 178 takes this information extracted by MEM 174 and generates emotion information with the corresponding image or video. The image and corresponding technical, descriptive, administrative and emotion metadata are then stored in image storage 182.

Figure 4:
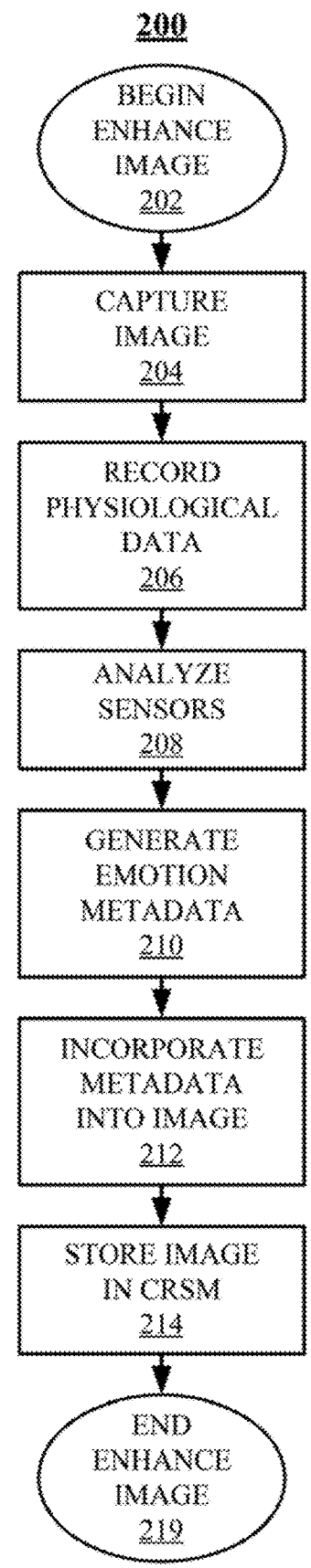
FIG. 4 is a flowchart of one example of an Enhance Image process that may implement aspects for the claimed subject matter.

FIG. 4 is a flowchart of one example of an Enhance Image process 200 that may implement aspects for the claimed subject matter. In this example, logic associated with process 200 is stored on CRSM 160 (FIG. 2) of smartphone 102 (FIG. 1) and executed on microcontroller 158 (FIG. 2). Although process 200 is described with respect to an image captured by smartphone 102 and it should be noted that process 200 is equally applicable to captured videos and other types of device.

Process 200 starts in a "Begin Enhance Image" block 202 and proceeds immediately to a "Capture Image" block 204. During processing associated with block 204, an image (or video) is captured by smartphone 102 via camera 104 (FIG. 1). After processing by signal processor 154 (FIG. 2) and sensor processor 156, the captured image would typically be stored as a digital file in computer-readable storage medium (CRSM) 160. During processing associated with a "Record Physiological Data" block 206, any physiological data detected by sensors 152 (FIG. 2) is also processed by signal processor 154 and sensor processor 156 and stored in CRSM 160. Typically, block 204 and 204 would be executed as close to concurrently as possible.

During processing associated with an "Analyze Sensors" block 208, both the captured image and sensor data captured during processing associated with blocks 204 and 206 is analyzed by SPL 157 (FIG. 2) to determine any emotion information that can be inferred from the image and data collected from, for example, a notebook computer, tablet computer, smart watch, sound recording device and so on. For example, a smiling face on an individual in the image may infer that the individual is happy while a frowning face would indicate unhappiness or disapproval.

During processing associated with a "Generate Emotion Metadata" block 210, the analysis generated during processing associated with block 208 is converted into metadata that may be stored in conjunction with the image stored during processing associated with block 204. During processing associated with an "Incorporate Metadata Into Image" block 212, the metadata generated during processing associated with block 212 is incorporated into, or associated with, the image captured during processing associated with block 204. During processing associated with a "Store Image in CRSM" block 214, the metadata and image are stored in CRSM 160 in a manner that enables them to be associated with each other, i.e., typically in a single file or in files that are linked to each other. Finally, during processing associated with an "End Enhance Image" block 219, process 200 is complete.

Figure 5:
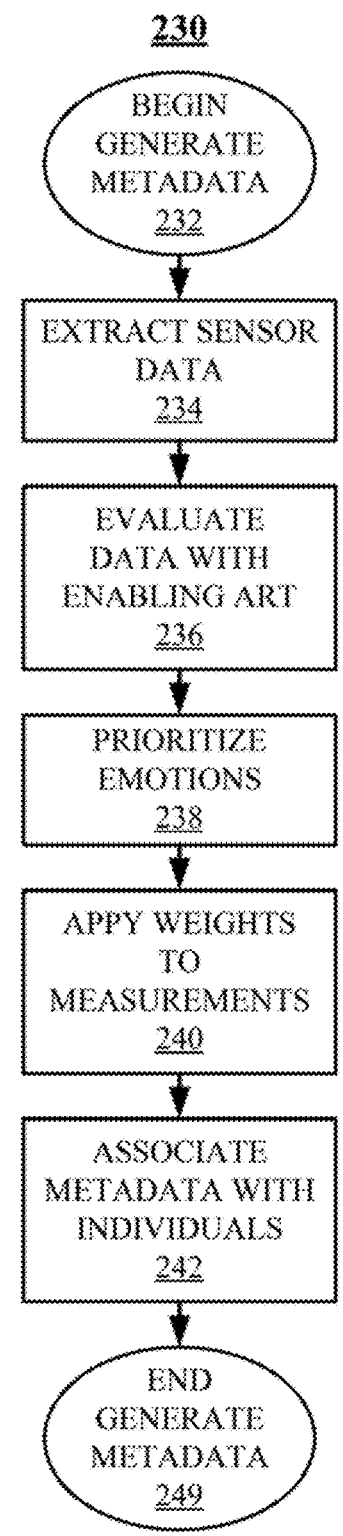
FIG. 5 is a flowchart of one example of a Generate Metadata process that may implement aspects for the claimed subject matter.

FIG. 5 is a flowchart of one example of a Generate Metadata process 230 that may implement aspects for the claimed subject matter. Process 230 corresponds to Generate Emotion Metadata block 210 (FIG. 4) of process 200 (FIG. 4). In this example, logic associated with process 200 is stored on CRSM 160 (FIG. 2) of smartphone 102 (FIG. 1) and executed on microcontroller 158 (FIG. 2). Process 230 starts in a "Begin Generate Metadata" block 232 and proceeds immediately to an "Extract Sensor Data" block 234. During processing associated with block 234, data collected by sensors 152 (FIG. 2) are associated with the particular sensor that collected each datum. During processing associated with an "Evaluate Data with Enabling Art" block 236, the collected data is evaluated based upon the particular type of sensor that recorded the data and emotion information is extracted.

Tools are available to make these types of determinations. For example, an EmoVu API, published by Eyeris of Palo Alto, Calif., is able to detect emotions on faces that appear in photographs and video. Devices and software are available to analyze audio data based upon both tone and content, thereby producing an emotion associated with the audio data. Other capabilities are able to provide automatic emotion recognition of general sounds. Sound clips from different areas of the daily human environment are selected and modeled using a dimensional approach in the emotional arousal and valence space. An "emotion mouse" (not shown), which may not be relevant with respect to smartphone 102 but could be employed with other types of devices, evaluates a user's emotion such as anger, fear, sadness, disgust, happiness, surprise, and so on when using a computer. The emotion mouse may measure both the behavior of the mouse as well as physiological data points such as, but not limited to, heartrate, skin temperature, skin moisture and skin conductivity.

During processing associated with a "Prioritize Emotions" block 238, elements of the emotion data are prioritized with respect to each other, i.e., data from different sensors are assigned relative importance. The basis of the prioritization is based upon user configurable parameters stored in conjunction with option data 186 (FIG. 3) of data module 174 (FIG. 3). During processing associated with an "Apply Weights to Measurements" block 240, different data from particular sensors may by weighted to be more or less influential determinations of an emotion analysis based upon the user configurable parameters stored in conjunction with option data 186.

During processing associated with an "Associate Metadata with Individuals" block 242, the emotion information generated during processing associated with blocks 234, 236, 238 and 240 is associated with the relevant individuals, which may include either an individual identified in the image captured during processing associated with block 204 (FIG. 4) of process 200 or the individual responsible for capturing the image. Finally, control proceeds to an "End Generate Metadata" block 249 in which process 230 is complete.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

We claim:

1. A method for enhancing images with emotion information, comprising:
capturing an image;
capturing physiological data corresponding to an individual that captures the image, wherein the physiological data comprises at least finger pressure of the individual during image capture of the image;
identifying an individual in the image;
analyzing the image for a first emotional content, wherein the analyzing comprises evaluating a facial expression of the individual and prioritizing emotions based on data from one or more sensors;
converting the first emotional content into emotion metadata;

correlating the first emotional content with the individual to produce a first associated emotion metadata;

storing the first associated emotion metadata in conjunction with the image in a computer-readable storage medium;

analyzing the physiological data for a second emotional content;

converting the second emotional content into a second emotion metadata; and storing the second emotion metadata in conjunction with the image in the computer-readable storage medium.

2. The method of claim 1, wherein the physiological data further comprises at least one of the following:

heartrate;

skin temperature;

skin conductivity;

skin electricity; and moisture.

3. The method of claim 1, wherein the method is implemented on a smartphone.

4. The method of claim 1, further comprising retrieving a subset of stored images with a search based upon the emotion metadata, wherein the subset of stored images has an individual emotional metadata associated with each individual image within the subset of stored images.

* * * * *